US012558302B2

(12) United States Patent
Martinez Gutierrez et al.

(10) Patent No.: US 12,558,302 B2
(45) Date of Patent: Feb. 24, 2026

(54) TYROSINASE-INHIBITING MOLECULES AND DERMOPHARMACEUTICAL COMPOSITION THAT INCLUDES THEM

(71) Applicant: MESOESTETIC PHARMA GROUP, S.L, Barcelona (ES)

(72) Inventors: Alfredo Martinez Gutierrez, Barcelona (ES); Alexandra Bertran Junque, Barcelona (ES); Maria del Carmen Gonzalez Rodriguez, Barcelona (ES); Sergio Pascual Del Prado, Barcelona (ES); Luis Shotze Luis Garcia, Barcelona (ES)

(73) Assignee: MESOESTETIC PHARMA GROUP, S.L, Barcelona (ES)

( * ) Notice: Subject to any disclaimer, the term of this patent is extended or adjusted under 35 U.S.C. 154(b) by 419 days.

(21) Appl. No.: 18/551,491

(22) PCT Filed: Apr. 1, 2021

(86) PCT No.: PCT/ES2021/070225

§ 371 (c)(1),
(2) Date: Sep. 20, 2023

(87) PCT Pub. No.: WO2022/129651

PCT Pub. Date: Jun. 23, 2022

(65) Prior Publication Data

US 2024/0197601 A1 Jun. 20, 2024

(51) Int. Cl.

| | |
|---|---|
| ***A61K 8/46*** | (2006.01) |
| ***A61K 31/12*** | (2006.01) |
| ***A61Q 19/00*** | (2006.01) |

(52) U.S. Cl.
CPC .............. *A61K 8/466* (2013.01); *A61K 31/12* (2013.01); *A61Q 19/00* (2013.01); *A61K 2800/782* (2013.01)

(58) Field of Classification Search
None
See application file for complete search history.

(56) References Cited

PUBLICATIONS

Nerya et al. "Chalcones as potent tyrosinase inhibitors: the effect of hydroxyl positions and numbers" Phytochemistry 65 (2004) 1389-1395 (Year: 2004).*

* cited by examiner

*Primary Examiner* — Adam C Milligan
*Assistant Examiner* — Jed A Kucharczk
(74) *Attorney, Agent, or Firm* — ALBERT BORDAS, P.A.

(57) ABSTRACT

The present invention provides tyrosinase-inhibiting molecules of general formula (I) and a dermopharmaceutical or cosmetic composition that includes at least one of said tyrosinase-inhibiting molecules.

(I)

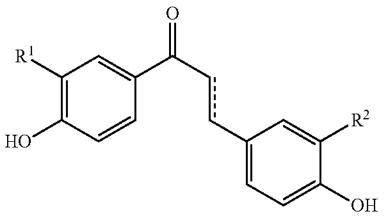

6 Claims, 1 Drawing Sheet

Figure 1

Percentage of tyrosinase activity of the molecules at a concentration of 1 mM. n=3 per group. * $p < 0.001$,  $p < 0.01$ and * $p < 0.05$, Student's T-Test. The error bars represent average ± standard deviation.

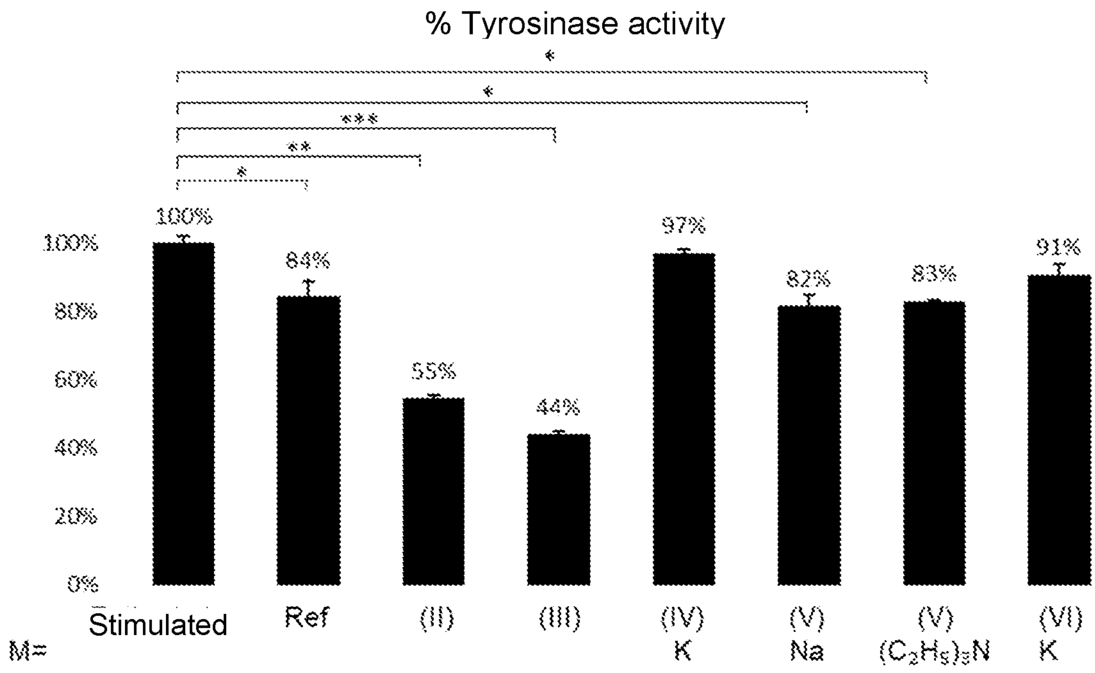

Figure 2

Percentage of reduction of melanin content of the molecules of formulas (II) and (III). n=3 per group. *** $p < 0.001$, indicates $p < 0.01$ and indicates $p < 0.05$, Student's T-Test. The error bars represent average ± standard deviation.

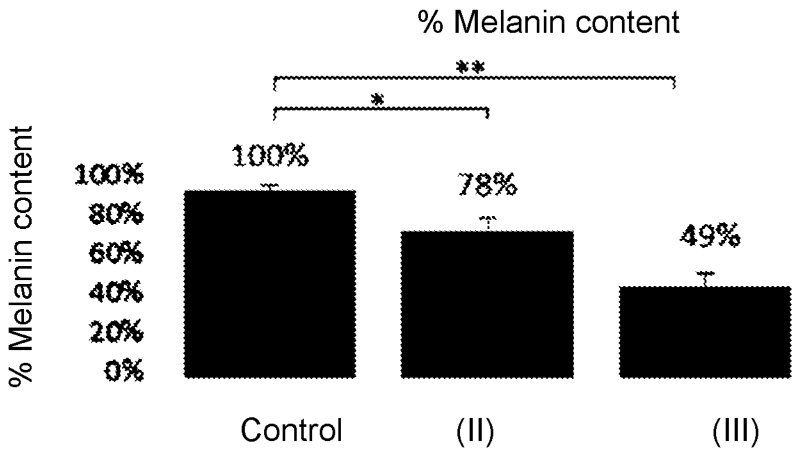

TYROSINASE-INHIBITING MOLECULES AND DERMOPHARMACEUTICAL COMPOSITION THAT INCLUDES THEM

The present invention relates to novel tyrosinase-inhibiting molecules and a dermopharmaceutical or cosmetic composition that includes at least one of said tyrosinase-inhibiting molecules.

More specifically, in a first aspect, the invention provides novel tyrosinase-inhibiting molecules with the following general formula (I):

(I)

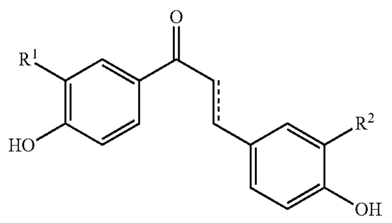

wherein $R^1$ and $R^2$ are selected, independently therebetween, from H, $HSO_3$ or one of their salts with a physiologically acceptable cation and ----- represents a single or double bond, wherein $R^1$ and $R^2$ do not represent both H, having high water solubility compared to other molecules which share the same structure.

In a second aspect, the invention provides a dermophamaceutical or cosmetic composition which comprises at least one tyrosinase-inhibiting molecule of general formula (I), as described above in combination with adequate excipients for the formulation thereof.

Skin pigmentation disorders consisting of melanin hyperproduction of melanin or hypermelanosis and melanin deficiency or hypomelanosis are frequent. Hypermelanosis appears more frequently in certain periods of life, usually caused by exogenous factors such as overexposure to sun. Hypermelanosis is characterised by the appearance of dark and coloured spots on the skin, particularly in exposed areas, which give them a certain degree of visual heterogeneity; it is generally an aesthetic problem. These spots are caused by melanocytic hypertrophy or by a greater accumulation of melanin in the keratinocytes located in the superficial part of the epidermis. Similarly, different dysfunctions of melanogenesis due to the effect of exogenous aggressions, for example hormonal or ageing alterations, trigger the appearance of dark, brown or blackish spots of melanic origin in the form of melasmas, ephelides, senescence spots, lentigo, etc.

Thus, for example, melasma is a topical condition consisting of increased pigmentation in the form of irregular, asymmetrical spots on localised areas of the skin, mainly sun-exposed areas. It is an acquired hypermelanosis characterised by reticulated, irregular, brown, asymmetrical spots in skin areas exposed to the sun, particularly the face. To date, melasma pathogenesis has not yet been fully elucidated. However, it has been proposed that chronic exposure to ultraviolet (UV) rays, feminine hormone stimulation and genetic background play a role in the development of melasma (O. A. Ogbechie-Godec, N. Elbuluk. Dermatol Ther (Heidelb) 2017, 7(3), 305). Management of melasma is challenging, mainly because it is susceptible to frequent relapses (Kwon S H, et al. Melasma: Updates and perspectives. Exp Dermatol. 2019; 28(6):704-708).

In the pigmentation process, the tyrosinase enzyme plays a key role in melanin synthesis, being the tyrosinase inhibitors an approximation widely used to treat hyperpigmentation conditions (Zolghadri S, et al. A comprehensive review on tyrosinase inhibitors. J Enzyme Inhib Med Chem. 2019; 34(1):279-309). Thus, since tyrosinase plays a key role in the melanin production process, inhibitors of this enzyme are often used as skin depigmenting agents.

In EP 1857109 A2, for example, phenyltiourea derivatives are disclosed as mammal tyrosinase inhibitors in cellular-free melanocyte or mammal melanoma cell extracts. EP 2117498 B1 discloses 4-hydroxyphenoyacetic acid derivatives for clearing and/or whitening the skin and/or for reducing pigmentation and/or for reducing hyperpigmentation and/or for inhibiting melanogenesis.

Among the different chemical families which act on this enzyme, chalcones have shown promising results, exhibiting a potent tyrosinase-inhibiting activity (Kostopoulou I, et al. Recent Developments on Tyrosinase Inhibitors based on the Chalcone and Aurone Scaffolds. Current Enzyme Inhibition. 2018; 14:3-17; Khatib S, et al. Chalcones as potent tyrosinase inhibitors: the importance of a 2,4-substituted resorcinol moiety. Bioorg Med Chem. 2005; 13(2):433-41).

However, these molecules, which are known tyrosinase inhibitors, are highly insoluble in water, which limits their use in cosmetic formulations.

In this context, it would be essential to find molecules which are effective tyrosinase inhibitors and also water soluble and, therefore, suitable for use in skincare products.

Thus, the objective of the present invention is to find molecules that meet these conditions based on the effectiveness of chalcones as depigmenting agents.

Based on the substructure of the chalcone family and the position of the hydroxyl groups, since it has been demonstrated that the location of these hydroxyl groups is key in tyrosinase inhibition by chalcones (Nerya O, et al., "Chalcones as potent tyrosinase inhibitors: the effect of hydroxyl positions and numbers". Phytochemistry. 2004; 65(10):1389-95), the present invention provides novel tyrosinase-inhibiting molecules with the following general formula (I):

(I)

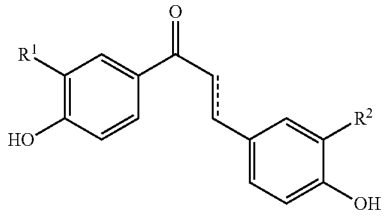

wherein $R^1$ and $R^2$ are selected, independently therebetween, from H, $HSO_3$ or one of their salts with a monovalent cation, $M^+SO_3^-$, or with any physiologically acceptable cation, and ----- represents a single or double bond, with the condition that $R^1$ and $R^2$ do not represent both H simultaneously, having high water solubility compared to other molecules which share the same structure and, therefore, are useful for use as depigmenting agents in skincare products.

In one embodiment, in the molecule of general formula (I), $R^1$ and $R^2$ are both $HSO_3$ and ----- is a double bond, in accordance with formula (II):

(II)

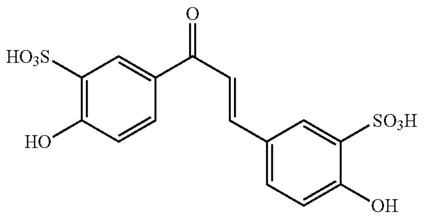

In another embodiment, in the molecule of general formula (I), wherein one of $R^1$ or $R^2$ is $HSO_3$, and the other of $R^1$ and $R^2$ is H and ----- is a double bond, in accordance with formula (III):

(III)

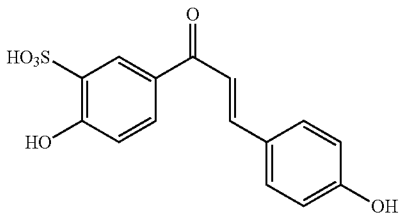

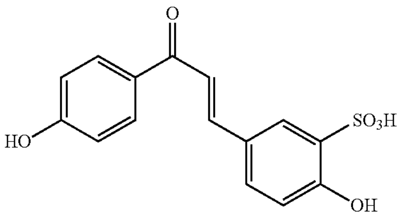

In another embodiment, in the molecule of general formula (I), $R^1$ and $R^2$ are both $M^+SO3^-$ and ----- is a single bond, in accordance with formula (IV):

(IV)

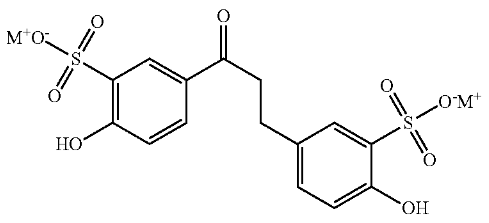

In a preferred embodiment of the compound of formula (IV), $M^+$ is a sodium, potassium or triethylammonium cation.

Similarly, in another embodiment, in the molecule of general formula (I), $R^1$ is $M^+SO_3^-$ and $R^2$ is H, ----- is a double bond, in accordance with formula (V):

(V)

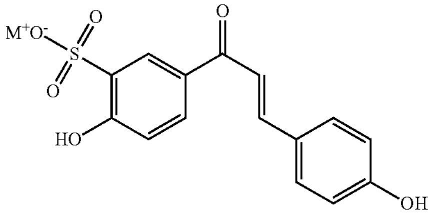

In a preferred embodiment of the compound of formula (V), M is a sodium, potassium or triethylammonium cation.

In a last embodiment, in the molecule of general formula (I), $R^1$ and $R^2$ are both $M^+SO_3^-$ and ----- is a double bond, in accordance with formula (VI):

(VI)

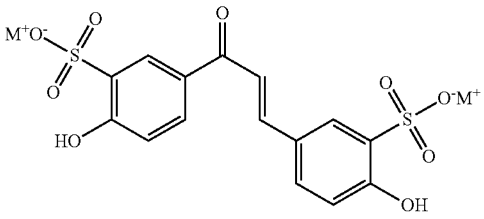

In a preferred embodiment of the compound of formula (VI), M is a sodium, potassium or triethylammonium cation.

In accordance with the second aspect of the invention, a dermopharmaceutical or cosmetic composition is provided which comprises at least one tyrosinase-inhibiting molecule of general formula (I), as described above in combination with adequate excipients for the formulation thereof.

In this context, embodiments of the dermopharmaceutical or cosmetic composition of the invention include the tyrosinase-inhibiting molecules of formula (I) or formulas (II) to (VI), alone or in combination with at least two of them, together with adequate excipients for the formulation thereof.

Preferably, the tyrosinase-inhibiting molecule is present in the dermopharmaceutical or cosmetic composition in a concentration of 0.001-25% by weight As mentioned earlier, the dermopharmaceutical or cosmetic composition of the invention includes adequate excipients for the formulation thereof for administration. Such excipients may be selected from oily solvents, anhydrous solvents, hydroalcoholic solvents, aqueous solvents, loads, preservatives, gelling agents, perfumes, surfactants, sunscreens, antioxidants, viscosifiers, emulsifiers, silicones and any of the ingredients used in the field of cosmetics or dermatology, in the usual concentrations for use, under the condition that said excipients do not interfere in the tyrosinase-inhibiting activity of the described combination.

The composition of the invention may appear in any galenic or cosmetic form of those normally used for application, for example, in the form of an aqueous, hydroalcoholic, hydroglycolic or oily solution. It can also be included in oil-in-water emulsions or be formulated like a serum, a foam or an aerosol.

The invention is illustrated below through the following examples, which are illustrative, but not limiting, thereof and in reference to the attached figures, wherein:

FIG. 1: Shows a graphic view of the tyrosinase activity, as a percentage, of the molecules of formula (II) to (VI) at a concentration of 1 mM.

FIG. 2: Shows a graphic view of the reduction percentage of the melamine content in human melanocyte simples treated with the molecules of formulas (II) and (III).

Effectiveness Of The Molecules Of General Formula (I)

Tyrosinase Inhibition

In order to assess the possible tyrosinase inhibition of these molecules, a computational human tyrosinase model based on known tyrosinase structures of other organisms was initially developed, since human tyrosinase has not crystallized and, therefore, its actual three-dimensional structure is not available.

This computational model was used with the aim of virtually assessing the similarity of the different structures of formula (I). A theoretical solubility study using log P was carried out parallel to a synthetic viability study of each.

Table 1 below shows the results obtained.

TABLE 1

| Structure | Average similarity (Kcal/mol) | LogP (ionic species) | LogP (non-ionic species) |
|---|---|---|---|
| 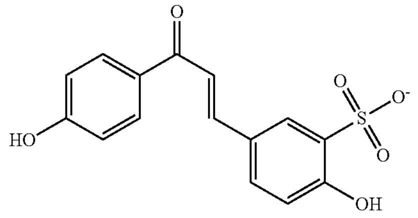 [SMILES: O=C(/C=C/c1ccc(O)c(S(=O)(=O)[O-])c1)c1ccc(O)cc1] | −8.0 | 0.74 | 3.11 |
| 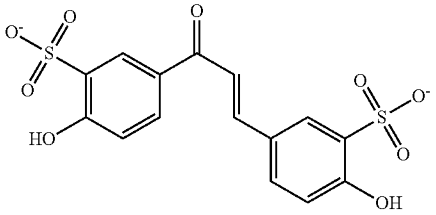 [SMILES: O=C(/C=C/c1ccc(O)c(S(=O)(=O)[O-])c1)c1ccc(O)c(S(=O)(=O)[O-])c1] | −8.1 | (−1.89 | (2.86) |

Given the results, an in vitro assay was conducted on human melanocytes. In order to stimulate melanogenic activity in the cells they were treated with L-tyrosine. This compound, in addition to being a substrate of the tyrosinase enzyme, key to melanin synthesis, is capable of activating cell receptors that activate the melanogenesis-regulating signalling pathways (Slominski A, et al. L-tyrosine and L-dihydroxyphenylalanine as hormone-like regulators of melanocyte functions. Pigment Cell Melanoma Res. 2012; 25(1):14-27). This condition is aimed at stimulating melanogenesis in melanocytes for the purpose of extracting tyrosinase and testing the effect of the molecules of the invention.

Thus, human melanocytes were cultured in culture medium (#PCS-200-013, ATCC) and L-tyrosine (2 mM) for 3 days. After the stimulation treatment, the cells were trypsinised and lysated in PBS pH 7.0 with 1% Triton X-100. The cell lysate, which contains tyrosinase, was incubated together with the molecules of the invention at different concentrations (0.1 and 1 mM), L-DOPA and MBTH (Winder A J and Harris H. New assays for the tyrosine hydroxylase and dopa oxidase activities of tyrosinase. Eur. J. Biochem. 1991; 198(2):317-26). L-DOPA acts as a substrate for tyrosinase in the enzyme reaction and MBTH is a compound that bonds to the hydroquinone formed from the oxidation of L-DOPA, generating a colour complex. Each of the conditions used was prepared in triplicate. Lastly, absorbance at 492 nm was monitored using a spectrophotometer every 10 min for 2-5 h.

The results obtained are shown in table 2 and FIG. 1. The L-tyrosine-stimulated control is considered 100% to establish a reference value. In the case of the samples treated with the different molecules, molecule (III) has lower tyrosinase activity (82% at 0.1 mM and 44% at 1 mM), followed by the molecule of formula (II) (97% at 0.1 mM and 55% at 1 mM). In the presence of the molecules of formulas (IV) to (VI), tyrosinase activity is reduced (97%, 82%, 83% and 91%, respectively, at 1 mM), but to a lesser extent in comparison with the first two molecules.

TABLE 1

Percentage of tyrosinase activity of the molecules synthesised at two differerent concentrations (0.1 and 1 mM)

| | Control | Reference | Stimulated + Molecule of formula | | | | | |
|---|---|---|---|---|---|---|---|---|
| | — | molecule | II | III | IV M = K | V M = Na | V M = $(C_2H_5)_3N$ | V M = K |
| 0.1 mM | 100 ± 2% | 97 ± 3% | 97 ± 0% | 82 ± 2% | >97% | >97% | >97% | >97% |
| 1 mM | | 84 ± 4% | 55 ± 1% | 44 ± 1% | 97 ± 1% | 82 ± 3% | 83 ± 0% | 91 ± 3% |

Reference molecule:

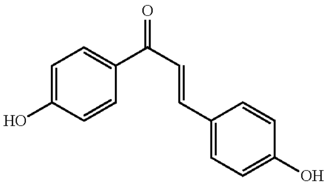 [SMILES: O=C(/C=C/c1ccc(O)cc1)c1ccc(O)cc1]

(E)-1,3-bis(p-hydroxyphenyl)-2-propen-1-one

Melanin Inhibition

With the aim of studying the inhibition of molecules in melanin, an in vitro assay was conducted on human melanocytes using similar conditions to those described in the tyrosinase inhibition assay. L-tyrosine is used to stimulate melanogenic activity in cells with the aim of extracting the melanin. Here, only the molecules with the best tyrosinase-inhibiting activity were tested (formulas (II) and (III)). In this experiment, the concentration of molecules used is the highest possible taking into account the melanocyte cytotoxicity value, 1.25 mM for the molecule of formula (II) and 0.33 mM for the molecule of formula (III).

Thus, human melanocytes are cultured in culture medium (#PCS-200-013, ATCC). L-tyrosine (2 mM) was added together with the molecule treatment. All the conditions were prepared in triplicate. After incubating the cells with the treatments for 3 days, they were trypsinised and lysated in 1M NaOH. Cell lysate absorbance at 340 nm was measured using a spectrophotometer. The absorbance value is directly proportional to melanin content.

As observed in FIG. 2, which shows the melanin content of the prepared samples, the L-tyrosine-stimulated control is considered 100% to establish a reference value. The difference between the melanin content of the samples treated with the molecules of formulas (II) (78±7%) and (III) (49±7%) and the sample treated only with L-tyrosine (100±3%) is significant, in accordance with Student's T-Test.

Solubility of the Synthesized Molecules

The following assay was conducted with the aim of studying and comparing the water solubility of the molecules.

Solutions are prepared in DMSO and in water for each of the molecules. All the samples are prepared at a final concentration of 50 mg/ml. After stirring for 1 hour at room temperature, the samples are filtered and a HPLC is performed.

In order to calculate the percentage of solubility of each of the molecules, the area of the peak of the sample dissolved in water and in DMSO obtained by HPLC is determined. The results are given as a percentage of solubility of the compound dissolved in water in the compound dissolved in DMSO.

Table 3 shows the results obtained. It can be observed that the reference molecule is fully water soluble at a concentration of 50 mg/ml. Molecules (II) and (III) are highly soluble at this concentration and the molecules of formulas (IV) to (VI) are fully water soluble at the tested concentration.

TABLE 2

Percentage of water solubility compared to the samples dissolved in DMSO

| | | Molecule of formula | | | | | |
|---|---|---|---|---|---|---|---|
| Concentration | Ref. | II | III | IV M = K | V M = Na | V M = $(C_2H_5)_3N$ | VI M = K |
| 50 mg/ml | 0% | 81% | 84% | 100% | 100% | 100% | 100% |

Synthesis of the Molecules of the Invention

Formula (II): 5-[(E)-2-(4-hydroxy-3-sulfobenzoyl)-1-ethenyl]-2-hydroxybenzenesulfonic Acid Under a nitrogen atmosphere, 1,039 g (4.33 mmol) of (E)-1,3-bis(p-hydroxyphenyl)-2-propen-1-one were slowly added to 5.04 g (43.3 mmol) of chlorosulfinic acid at 0° C. The reaction was maintained at room temperature for 22 h and the resulting mixture was slowly added to 25 ml of cold water. The aqueous phase obtained was extracted twice with 20 ml of ethyl acetate, the combined organic phases were washed with 10 ml of water and concentrated to dryness, to obtain 2,017 g of a solid containing 5-[(E)-2-(4-hydroxy-3-sulfobenzoyl)-1-ethenyl]-2-hydroxybenzenesulfonic acid (86.3% HPLC area).

1H NMR (d-DMSO, 360 MHZ): δ 6.86 (d, 1H), 6.91 (d, 1H), 7.62 (d, 1H), 7.70 (d, 1H), 7.82 (d, 1H), 7.86 (s, 1H), 8.14 (s, 1H), 8.21 (s, 1H).

Formula (III): 5-[(E)-3-(p-hydroxyphenyl)acryloyl]-2-hydroxybenzenesulfonic Acid 5-acetyl-2-hydroxybenzenesulfonic Acid (Synthesis Intermediate)

2 g (14.69 mmol) of 1-(p-hydroxyphenyl)-1-ethanone were slowly added to 17.6 g (146.9 mmol) of chlorosulfonic acid at 0° C. After 18 h at room temperature, 75 ml of cold water were added to the mixture and the mixture was extracted twice with 50 ml of ethyl acetate. The organic phase was vacuum concentrated to dryness to obtain 1.95 g of a raw product containing 1.71 g (54% yield) 5-acetyl-2-hydroxybenzenesulfonic acid and 0.24 g of 1-(p-hydroxyphenyl)-1-ethanone.

1H NMR (d-DMSO, 360 MHz): δ 2.50 (3H), 6.88 (d, 1H), 7.84 (d, 1H), 8.06 (s, 1H).

5-[(E)-3-(p-hydroxyphenyl)acryloyl]-2-hydroxybenzenesulfonic Acid 1.61 ml (26 mmol) of 98% sulphuric acid were slowly added to a mixture of 563 mg (2.60 mmol) of the previous raw product and 362 mg (2.60 mmol) of p-hydroxybenzaldehyde in 6.4 mL of ethanol at 0° C. The reaction was maintained at room temperature for 21 h and the mixture obtained was slowly added to a solution of 2 g sodium chloride in 10 ml of water at 0° C. The suspension was extracted twice with 20 ml of ethyl acetate and the combined organic phases were treated with anhydrous sodium sulphate and were concentrated to dryness. The product obtained was purified in a column with silica gel, eluting with a 100% dichloromethane to cichloromethane/methanol gradient of 8:2 to obtain 230 mg (27.6% yield) of 5-[(E)-3-(p-hydroxyphenyl)acryloyl]-2-hydroxybenzenesulfonic acid.

1H NMR (d-DMSO, 360 MHZ): δ 6.80-6.88 (2H), 6.91-6.97 (1H), 7.61-7.69 (2H), 7.69-7.78 (1H), 8.06-8.15 (1H), 8,18-8.25 (1H).

Formula (IV) (M=K): 5-[(E)-2-(4-hydroxy-3-sulfonatebenzoyl)-1-ethenyl]-2-hydroxybenzenesulfonate, Dipotassium Salt Under a nitrogen atmosphere, 20.8 g (86.63 mmol) of (E)-1,3-bis(p-hydroxyphenyl)-2-propen-1-one were slowly added to 138.25 g (1.18 mol) of chlorosulfonic acid at 0° C. The reaction was maintained at room temperature for 19 h and the resulting mixture was slowly added to 650 ml of cold water. The aqueous phase obtained was extracted twice with 500 ml of ethyl acetate, the combined organic phases were washed with 250 ml of water and were concentrated to dryness to obtain 60.66 g of a product containing 66% of 5-[(E)-2-(4-hydroxy-3-sulfobenzoyl)-1-ethenyl]-2-hydroxybenzenesulfonic acid. 60.1 g of this product were suspended in 230 ml of water and an equimolar amount of potassium carbonate was slowly added to obtain a complete solution. 600 ml of 2-propanol were added to obtain a suspension. The solid was filtered, washed twice with 200 ml of 2-propanol and was vacuum dried at 100° C. to constant weight, to obtain 19 g (46% yield) of dipotassium salt of 5-[(E)-2-(4-hydroxy-3-sulfonatebenzoyl)-1-ethenyl]-2-hydroxybenzenesulfonate.

1H NMR (d-DMSO, 360 MHZ): δ 6.86 (d, 1H), 6.91 (d, 1H), 7.63 (d, 1H), 7.71 (d, 1H), 7.82 (d, 1H), 7.87 (s, 1H), 8.15 (s, 1H), 8.22 (s, 1H), 10.98 (brs, 1H), 11.18 (brs, 1H).

Formula (V) (M=Na): 5-[(E)-3-(p-hydroxyphenyl)acryloyl]-2-sodium Hydroxybenzenesulfonate 1 g of 5-[(E)-3-(4-hydroxyphenyl)acryloyl]-2-hydroxybenzenesulfonic acid (3.12 mmol) was dissolved in 10 ml of 2-propanol and an equimolar amount of sodium bicarbonate was slowly added. The solid was filtered, washed twice with 2 ml of 2-propanol and vacuum dried to 50° C. to constant weight, obtaining 284 mg (27% yield) of 5-[(E)-3-(p-hydroxyphenyl)acryloyl]-2-sodium hydroxybenzenesulfonate.

1H NMR (d-DMSO, 360 MHZ): δ 6.80-6.88 (2H), 6.91-6.97 (1H), 7.61-7.69 (2H), 7.69-7.78 (1H), 8.06-8.15 (1H), 8.18-8.25 (1H), 10.98 (brs, 1H).

Formula (V) (M=$(C_2H_5)_3N$): 2-hydroxy-5-[2-(4-hydroxy-3-sulfonatebenzoyl)ethyl]-triethylammonium Benzenesulfonate 10 g of 5-[(E)-3-(4-hydroxyphenyl)acryloyl]-2-hydroxybenzenesulfonic acid (31.23 mmol) were dissolved in 70 ml of 2-propanol and 13.05 ml of trimethylamine (93.69 mmol) were slowly added. The solid was filtered, washed twice with 20 ml of 2-propanol and vacuum dried at 50° C. to constant weight, obtaining 10.6 g (81% yield) of 5-[(E)-3-(p-hydroxyphenyl)acryloyl]-2-triethylammonium hydroxybenzenesulfonate.

1H NMR (d-DMSO, 360 mHz): δ 1.06 (t, 9H), 2.80 (q, 6H), 6.83 (d, 2H), 6.93 (d, 1H), 7.66 (s, 2H), 7.73 (d, 2H), 8.09 (dd, 1H), 8.21 (d, 1H).

Formula (VI) (M=K): 2-hydroxy-5-[2-(4-hydroxy-3-sulfonatebenzoyl)ethyl]-benzenesulfonate, Dipotassium Salt In a high-pressure reactor, 1 g (2,10 mmol) of 5-[(E)-2-(4-hydroxy-3-sulfonatebenzoyl)-1-ethenyl]-2-hydroxybenzenesulfonate, dipotassium salt, was dissolved in 10 ml of water. 150 mg of Pd/C 10% were added and the mixture was hydrogenated at atmospheric pressure and 1,500 RPM for 72 h at room temperature. The reaction was controlled by 1H NMR. The reaction mixture was filtered through a layer of Celite® and concentrated to dryness, obtaining 2-hydroxy-5-[2-(4-hydroxy-3-sulfonatebenzoyl)ethyl]benzenesulfonate, dipotassium salt.

1H NMR (d-DMSO, 360 MHZ): δ 2.80 (t, 2H), 3.20 (t, 2H), 6.66 (d, 1H), 6.86 (d, 1H), 7.10 (d, 1H), 7.32 (s, 1H), 7.89 (d, 1H), 8.08 (s, 1H), 10.36 (brs, 1H), 11.12 (brs, 1H).

Reference Molecule: (E)-1,3-bis(p-hydroxyphenyl)-2-propen-1-one 16.06 g (165 mmol) of 98% sulphuric acid were slowly added to a mixture of 2 g (16.38 mmol) of p-hydroxybenzaldehyde and 2.23 g (16.38 mmol) of 1-(p-hydroxyphenyl)-1-ethanone in 20 ml of ethanol at room temperature. The reaction was maintained at room temperature for 23 h and the mixture obtained was slowly added to a solution of 10 g of sodium chloride in 33 ml of water at 0° C. The suspension was extracted three times with 16 ml of ethyl acetate and the combined organic phases were washed twice with 16 ml of water. After treating with anhydrous sodium sulphate, the organic phase was vacuum concentrated to dryness to obtain 3.58 g (91% yield, 97.4% HPLC area) of (E)-1.3-bis(p-hydroxyphenyl)-2-propen-1-one.

1H NMR (d-DMSO, 360 mHz): δ 6.33 (d, 1H), 6.71 (d, 2H), 7.45 (s, 2H), 7.51 (d, 2H), 7.76 (dd, 1H), 8.21 (d, 1H).

Sample Compositions of the Invention in Cream Form

| Components | % by weight |
|---|---|
| Molecules of the invention | 0.001-25 |
| Glycerine | 3 |
| Butylene glycol | 2 |

-continued

| Components | % by weight |
|---|---|
| Disodium EDTA | 0.1 |
| Niacinamide | 5 |
| Ethylhexylglycerine | 0.1 |
| Phenoxyethanol | 0.9 |
| Citric acid | 0.3 |
| Sodium citrate | 1.88 |
| Xanthan gum | 0.2 |
| Polyacrylate Crosspolymer-6 | 0.8 |
| Caprylic/capric triglyceride acid | 5 |
| Isonyl isononanoate | 2 |
| Isodecyl neopentanoate | 5 |
| Steareth-2 | 1 |
| Glyceryl stearate, PEG 100 stearate | 2 |
| Phosphate cetyl | 2 |
| Dimethicone | 2 |
| Cetylic alcohol | 2 |
| Pentaerythrityl tetra-di-t-butyl hydroxyhydrocinnamate | 0.1 |
| Plankton extract | 2 |
| Aminoethylphosphinic acid | 1 |
| Acetyl glycyl beta-alanine | 0.5 |
| Salicylic acid | 0.5 |
| Lactic acid | 1 |
| Perfume | 0.3 |
| Water | Up to 100% |

Sample Compositions of the Invention in Serum Form

| Components | % by weight |
|---|---|
| Molecules of the invention | 0.001-25 |
| Glycerine | 8 |
| Butylene glycol | 10 |
| Disodium EDTA | 0.1 |
| Niacinamide | 5 |
| Ethylhexylglycerine | 0.1 |
| Phenoxyethanol | 0.9 |
| Citric acid | 0.3 |
| Sodium citrate | 1.88 |
| Sodium metabisulfite | 0.2 |
| Polyacrylate Crosspolymer-6 | 1.5 |
| 1,3-propanedyol | 6 |
| TRIDECETH-9, PEG-40-hydrogenated castor oil, Polysorbate 20 | 1.5 |
| Potassium azeloyl diglycinate | 5 |
| Ascorbyl glucoside | 3 |
| Acetylglucosamine | 1 |
| Lepidium sativum extract | 2 |
| Water | Up to 100% |

The invention claimed is:

1. Tyrosinase-inhibiting molecules of the following general formula (I):

(I)

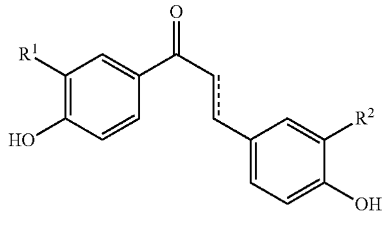

wherein $R^1$ and $R^2$ are selected, independently, from H, $HSO_3$ or one of their salts with a monovalent cation, $M^+SO_3^-$, or with any physiologically acceptable cation, and ------ represents a single or double bond, with the condition that $R^1$ and $R^2$ do not represent both H simultaneously.

2. Tyrosinase-inhibiting molecules, according to claim 1, selected from the following formulas (II) to (VI):

II

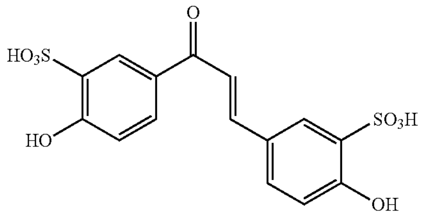 [SMILES: O=C(/C=C/c1ccc(O)c(S(=O)(=O)O)c1)c1ccc(O)c(S(=O)(=O)O)c1]

$R^1$ and $R^2$ are both $HSO_3$ and ------ is a double bond

III

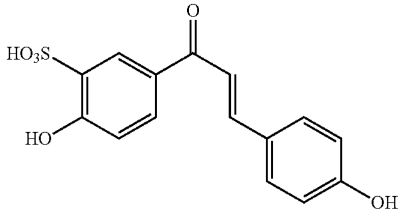 [SMILES: O=C(/C=C/c1ccc(O)cc1)c1ccc(O)c(S(=O)(=O)O)c1]

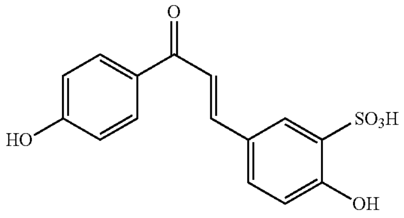 [SMILES: O=C(/C=C/c1ccc(O)c(S(=O)(=O)O)c1)c1ccc(O)cc1]

one of $R^1$ or $R^2$ is $HSO_3$, and the other of $R^1$ and $R^2$ is H and ------ is a double bond

IV

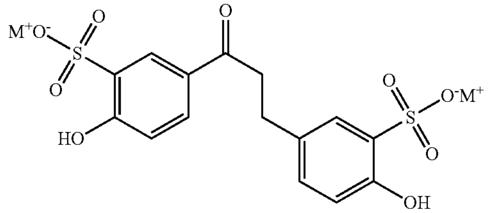

$R^1$ and $R^2$ are both $M^+SO_3^-$ and ------ is a single bond

V

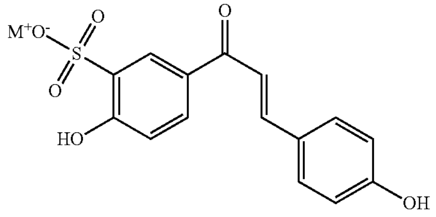

$R^1$ is $M^+SO_3^-$ and $R^2$ is H, ------ is a double bond

VI

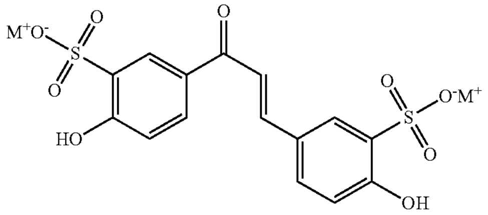

$R^1$ and $R^2$ are both $M^+SO_3^-$ and $\overline{\underline{-----}}$ is a double bond.

3. Tyrosinase-inhibiting molecules, according to claim 1 or 2, wherein M is sodium, potassium or triethylammonium.

4. A dermopharmaceutical or cosmetic composition which comprises at least one tyrosinase-inhibiting molecule of general formula (I), according to claim 1, in combination with adequate excipients for the formulation thereof.

5. The dermopharmaceutical or cosmetic composition which comprises at least one tyrosinase-inhibiting molecule selected from formulas (II) to (VI), according to claim 2, in combination with adequate excipients for the formulation thereof.

6. The dermopharmaceutical or cosmetic composition, according to claim 4 or 5, wherein the tyrosinase-inhibiting molecule is present in the dermopharmaceutical or cosmetic composition in a concentration of 0.001-25% by weight.

* * * * *